(12) United States Patent
Elebring et al.

(10) Patent No.: US 6,576,626 B2
(45) Date of Patent: Jun. 10, 2003

(54) AMINOPROPYLPHOSPHINIC ACIDS

(75) Inventors: Thomas Elebring, Pixbo (SE); Peter Guzzo, Niskayuna, NY (US); Marianne Swanson, Mölndal (SE); Sverker Von Unge, Fjärås (SE)

(73) Assignee: AstraZeneca AB, Sodertalje (SE)

( * ) Notice: Subject to any disclaimer, the term of this patent is extended or adjusted under 35 U.S.C. 154(b) by 117 days.

(21) Appl. No.: 09/786,219

(22) PCT Filed: Dec. 4, 2000

(86) PCT No.: PCT/SE00/02426
§ 371 (c)(1),
(2), (4) Date: Mar. 1, 2001

(87) PCT Pub. No.: WO01/42252
PCT Pub. Date: Jun. 14, 2001

(65) Prior Publication Data
US 2002/0156053 A1 Oct. 24, 2002

(30) Foreign Application Priority Data

Dec. 9, 1999 (SE) .............................................. 9904508
Oct. 9, 2000 (SE) .............................................. 0003640

(51) Int. Cl.⁷ ............................................ A61K 31/662
(52) U.S. Cl. ...................................... 514/114; 562/11
(58) Field of Search ...................... 514/75, 114; 562/8, 562/11; 568/841; 564/305, 336, 355; 560/157, 231

(56) References Cited

U.S. PATENT DOCUMENTS

| | | | |
|---|---|---|---|
| 4,740,332 A | * 4/1988 | Thottathil | 560/130 |
| 5,004,826 A | * 4/1991 | Dingwall et al. | 558/166 |
| 5,036,057 A | 7/1991 | Martin | 514/54 |
| 5,229,379 A | * 7/1993 | Marescaux et al. | 514/114 |
| 5,281,747 A | 1/1994 | Hall et al. | 562/11 |
| 5,332,729 A | * 7/1994 | Mickel et al. | 514/114 |
| 5,407,922 A | * 4/1995 | Marescaux et al. | 514/114 |
| 5,461,040 A | 10/1995 | Hall et al. | 514/114 |
| 5,538,956 A | * 7/1996 | Minchin et al. | 514/114 |
| 5,567,840 A | 10/1996 | Hall et al. | 562/11 |
| 6,117,908 A | * 9/2000 | Andrews et al. | 514/114 |

FOREIGN PATENT DOCUMENTS

| | | |
|---|---|---|
| CH | 449046 | 4/1968 |
| EP | 0181833 | 5/1986 |
| EP | 0356128 | 2/1990 |
| EP | 0399949 | 11/1990 |
| EP | 0463969 | 1/1992 |
| FR | 2722192 | 1/1996 |
| WO | 8704077 | 7/1987 |
| WO | 9611680 | 4/1996 |
| WO | 9811885 | 3/1998 |

OTHER PUBLICATIONS

Froestl, et al. (1995), J. Med. Chem., 38, 3297–3312.
Zukin, et al. (1974), Proc. Natl. Acad. USA 71, 4802–4807.
Olpe et al. (1990), Eur. J. Pharmacol. 187, 27–38.
Holloway & Dent (1990), Gastroenterol. Clin. N. Amer. 19, 517–535.
The GABA Receptors; Second Edition, Edited by S.J. Enna and Norman Bowery, Humana Press (1997), pp. 281–282.
U.S. patent application Ser. No. 09/786,220, Amin et al., filed Mar. 1, 2001.

* cited by examiner

Primary Examiner—Jean F. Vollano
(74) Attorney, Agent, or Firm—White & Case LLP

(57) ABSTRACT

Novel compounds of formula I, with the exception of i) the racemate of (3-amino-2-hydroxypropyl)phosphinic acid; and ii) (2R/S, 3R)-(3-amino-2-hydroxybutyl)phosphinic acid, having affinity to one or more $GABA_B$ receptors, their pharmaceutically acceptable salts, solvates and stereoisomers, as well as processes for their preparation, pharmaceutical compositions containing said therapeutically active compounds and the use of said active compounds in therapy $$R_4\overset{H}{\underset{}{N}}-\underset{R_3}{\overset{R_2}{C}}-\underset{R_1}{C}-\overset{O}{\underset{OH}{P}}-H \quad (I)$$

11 Claims, No Drawings

AMINOPROPYLPHOSPHINIC ACIDS

This is a 371 of PCT SE00/02426 filed Dec. 4, 2000, now No. 01/42252

FIELD OF THE INVENTION

The present invention is related to novel compounds having affinity to one or more $GABA_B$ receptors, as well as to their pharmaceutically acceptable salts, solvates and stereoisomers. The invention is also related to processes for their preparation, pharmaceutical compositions containing said therapeutically active compounds and to the use of said active compounds in therapy.

BACKGROUND AND PRIOR ART

Reflux

Gastro-oesophageal reflux disease (GORD) is the most prevalent upper gastrointestinal tract disease. Current therapy has aimed at reducing gastric acid secretion, or at reducing oesophageal acid exposure by enhancing oesophageal clearance, lower oesophageal sphincter tone and gastric emptying. The major mechanism behind reflux has earlier been considered to depend on a hypotonic lower oesophageal sphincter. However recent research (e.g. Holloway & Dent (1990) *Gastroenterol. Clin. N. Amer.* 19, 517–535) has shown that most reflux episodes occur during transient lower oesophageal sphincter relaxations, hereinafter referred to as TLOSR, i.e. relaxations not triggered by swallows. It has also been shown that gastric acid secretion usually is normal in patients with GORD.

Consequently, there is a need for compounds which reduce the incidence of TLOSR and thereby prevent reflux.

Pharmaceutical compositions comprising a local anaesthetic, adapted to inhibit relaxation of the lower oesophageal sphicter are disclosed in WO 87/04077 and in U.S. Pat. No. 5,036,057. Recently $GABA_B$-receptor agonists have been shown to inhibit TLOSR which is disclosed in WO 98/11885.

$GABA_B$ Receptor Agonists

GABA (4-aminobutanoic acid) is an endogenous neurotransmitter in the central and peripheral nervous systems. Receptors for GABA have traditionally been divided into $GABA_A$ and $GABA_B$ receptor subtypes. $GABA_B$ receptors belong to the superfamily of G-protein coupled receptors. $GABA_B$ receptor agonists are being described as being of use in the treatment of CNS disorders, such as muscle relaxation in spinal spasticity, cardiovascular disorders, asthma, gut motility disorders such as irritable bowel syndrome (IBS) and as prokinetic and anti-tussive agents. $GABA_B$ receptor agonists have also been disclosed as useful in the treatment of emesis (WO 96/11680) and recently, as mentioned above, in the inhibition of TLOSR (WO 98/11885).

The most studied $GABA_B$ receptor agonist is baclofen (4-amino-3-(chlorophenyl)butanoic is acid) disclosed in the Swiss patent No. CH 449, 046. Baclofen has for several years been used as an antispastic agent. EP 0356128 describes the use of the specific compound (3-aminopropyl) methylphosphinic acid, as a potent $GABA_B$ receptor agonist, in therapy. EP 0181833 discloses substituted 3-aminopropylphosphinic acids which are found to have very high affinities towards $GABA_B$ receptor sites. In analogy to baclofen, the compounds can be used as for instance muscle relaxants. EP 0399949 discloses derivatives of (3-aminopropyl)methylphosphinic acid which are described as potent $GABA_B$ receptor agonists. These compounds are stated to be useful as muscle relaxants. EP 0463969 and FR 2722192 are both applications related to 4-aminobutanoic acid derivatives having different heterocyclic substituents at the 3-carbon of the butyl chain. Structure-activity relationships of several phosphinic acid analogues with respect to their affinities to the $GABA_B$ receptor as well as their muscle relaxant effect are discussed in *J. Med. Chem.* (1995), 38, 3297–3312. The conclusion in said article is that considerably stronger muscle relaxation could be achieved with the (S)-enantiomer of 3-amino-2-hydroxypropylmethylphosphinic acid than with baclofen and without the occurrence of unwanted CNS effects.

In literature the phosphinic acids having a hydrogen atom attached to phosphorous also are named phosphonous acids. These are two names for the same compounds and both names can be used. However, we have chosen to use the name phosphinic acids for the compounds according to the present invention.

OUTLINE OF THE INVENTION

The present invention provides novel compounds of the formula I

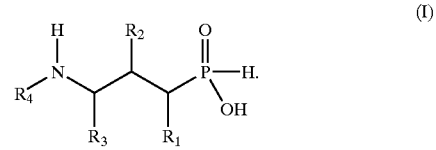

wherein
  $R_1$ represents hydrogen, hydroxy, lower alkyl, lower alkoxy or halogen;
  $R_2$ represents hydroxy, mercapto, halogen, or an oxo group;
  $R_3$ represents hydrogen or lower alkyl (optionally substituted with hydroxy, mercapto, lower alkoxy, lower thioalkoxy or aryl);
  $R_4$ represents hydrogen, lower alkyl (optionally substituted with aryl), or aryl;
  and pharmaceutically acceptable salts, solvates and the stereoisomers thereof,
  with the exceptions of:
    i) the racemate of (3-amino-2-hydroxypropyl) phosphinic acid, and
    ii) (2R/S, 3R)-(3-amino-2-hydroxybutyl)phosphinic acid.
  In a preferred embodiment
  $R_1$ represents hydrogen, a lower alkyl or halogen;
  $R_2$ represents halogen, hydroxy or an oxo group;
  $R_3$ represents hydrogen; and
  $R_4$ represents hydrogen;
  with the exception of the racemate of (3-amino-2-hydroxypropyl)phosphinic acid.
  Even more preferred compounds are (3-amino-2-fluoropropyl)phosphinic acid, (2R)-(3-amino-2-fluoropropyl)phosphinic acid, (2S)-(3-amino-2-fluoropropyl)phosphinic acid, (3-amino-2-fluoro-1-methylpropyl)phosphinic acid, (3-amino-2-oxopropyl) phosphinic acid, (2S)-(3-amino-2-hydroxypropyl) phosphinic acid, (2R)-(3-amino-2-hydroxypropyl)

phosphinic acid and (3-amino-1-fluoro-2-hydroxypropyl) phosphinic acid.

Within the scope of the invention, it is to be understood that when $R_2$ is an oxo group the bond between $R_2$ and the carbon is a double bond.

Within the scope of the invention, it is to be understood by "lower" radicals and compounds, for example, those having up to and including 7, especially up to and including 4, carbon atoms. Also the general terms have the following meanings:

Lower alkyl is, for example, $C_1$–$C_4$ alkyl, such as methyl, ethyl, n-propyl or n-butyl, also isopropyl, isobutyl, secondary butyl or tertiary butyl, but may also be a $C_5$–$C_7$ alkyl group such as a pentyl, hexyl or heptyl group.

Lower alkoxy is, for example, $C_1$–$C_4$ alkoxy, such as methoxy, ethoxy, n-propoxy or n-butoxy, also isopropoxy, isobutoxy, secondary butoxy or tertiary butoxy, but may also be a $C_5$–$C_7$ alkoxy group, such as a pentoxy, hexoxy or heptoxy group.

Lower thioalkoxy is, for example, $C_1$–$C_4$ thioalkoxy, such as thiomethoxy, thioethoxy, n-thiopropoxy or n-thiobutoxy, also thioisopropoxy, thioisobutoxy, secondary thiobutoxy or tertiary thiobutoxy, but may also be a $C_5$–$C_7$ thioalkoxy group, such as a thiopentoxy, thiohexoxy or thioheptoxy group.

Halogen is halogen of atomic number up to and including 35, such as fluorine or chlorine and less preferred bromine.

The compounds according to formula I of the invention are of amphoteric nature and may be presented in the form of internal salts. They can also form acid addition salts and salts with bases. Such salts are particularly pharmaceutically acceptable acid addition salts, as well as pharmaceutically acceptable salts formed with bases. Suitable acids for the formation of such salts include, for example, mineral acids such as hydrochloric, hydrobromic, sulfuric, or phosphoric acid or organic acids such as sulfonic acids and carboxylic acids. Salts with bases are, for example, alkali metal salts, e.g. sodium or potassium salts, or alkaline earth metal salts, e.g. calcium or magnesium salts, as well as ammonium salts, such as those with ammonia or organic amines. The salts may be prepared by conventional methods.

When one or more stereocentre is present in the molecule, the compounds according to formula I can be in the form of a stereoisomeric mixture, i.e. a mixture of diastereomers and/or racemates, or in the form of the single stereoisomers, i.e. the single enantiomer and/or diastereomer. The compounds can also be in the form of solvates, e.g. hydrates.

All of the compounds according to the formula I can be used for the inhibition of TLOSR, and thus for the treatment of gastro-oesophageal reflux disease. The said inhibition of TLOSR also implies that the said compounds of formula I can be used for the treatment of regurgitation in infants. Effective management of regurgitation in infants would be an important way of managing failure to thrive due to excessive loss of ingested nutrient. Furthermore the novel compounds can be used for the treatment of GORD-related or non-GORD related asthma, belching, coughing, pain, cocaine addiction, hiccups, IBS, dyspepsia, emesis and nociception.

As opposed to what is stated in prior art, (*J. Med. Chem.* (1995) 3297–3312 and *The GABA Receptors; Second Edition*, Edited by S. J Enna and Norman Bowery, Humana Press (1997) especially p. 281–282), the compounds according to the invention have surprisingly high metabolic stability in spite of the presence of a P—H bond. The compounds also possess a surprisingly high therapeutic index.

PREPARATION

The compounds according to formula I of the present invention may be prepared by one of the following methods.

A) A Compound of Formula II

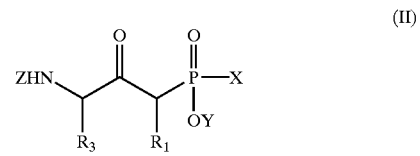

(II)

in which $R_1$ and $R_3$ are as defined above in formula I, X is hydrogen or a protecting group such as —CCH$_3$(OCH$_2$CH$_3$)$_2$, Z is a protecting group such as t-butyloxycarbonyl and Y is hydrogen or a protecting group such as lower alkyl, which compound of formula II may have been synthesized by a condensation reaction according to Scheme 1 employing an appropriate N-protected amino acid ester in which $R_3$ is as defined above, W is a protecting group such as lower alkyl and Z is as defined in formula II, and a suitable protected phosphinic acid derivative in which $R_1$ is as defined above in formula I, X and Y are as defined in formula II, and a base such as lithium diisopropylamide, Scheme 1

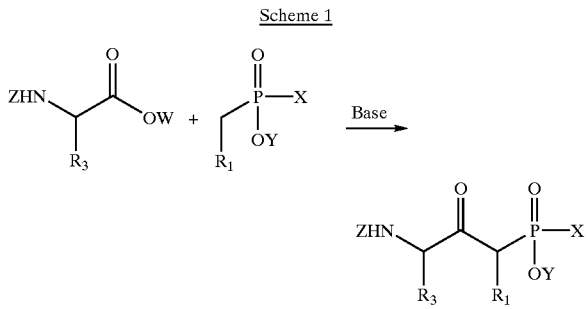

is a) optionally converted by an N-alkylation reaction in order to introduce $R_4$ if $R_4$ is desired to be not equal to hydrogen, and thereafter a hydrolytic reaction to obtain a compound of formula III

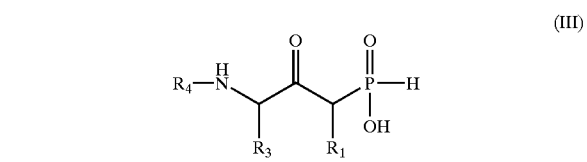

(III)

wherein $R_1$, $R_3$ and $R_4$ are as defined above in formula I, and optionally convert the above resulting compound III into another chemical compound of the formula III and/or sepatate a resulting mixture of isomers into the individual isomers and/or convert a resulting salt into the free compound of the formula III and/or into another salt and/or convert a resulting free compound of the formula III into a salt to correspond to the above definition, or b) converted by a reductive reaction, optionally an N-alkylation reaction if $R_4$ is desired to be not equal to hydrogen, and finally a hydrolytic reaction to obtain a compound of formula IV

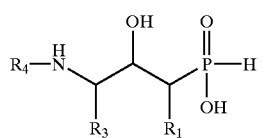
(IV)

wherein $R_1$, $R_3$ and $R_4$ are as defined above in formula I, and optionally convert the above resulting compound IV into another chemical compound of the formula IV and/or sepatate a resulting mixture of isomers into the individual isomers and/or convert a resulting salt into the free compound of the formula IV and/or into another salt and/or convert a resulting free compound of the formula IV into a salt to correspond to the above definition, or c) converted by a reductive reaction followed by a deoxohalogenation reaction, optionally an N-alkylation reaction in order to introduce $R_4$ if $R_4$ is desired to be not equal to hydrogen, and finally a hydrolytic reaction to obtain a compound of formula V

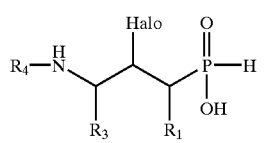
(V)

wherein $R_1$, $R_3$ and $R_4$ are as defined above in formula I and Halo is a halogen atom, and optionally convert the above resulting compound V into another chemical compound of the formula V and/or sepatate a resulting mixture of isomers into the individual isomers and/or convert a resulting salt into the free compound of the formula V and/or into another salt and/or convert a resulting free compound of the formula V into a salt to correspond to the above definition; or B) A Compound of Formula VI

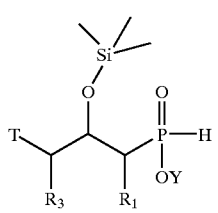
(VI)

in which $R_1$, and $R_3$ are as defined above in formula I, X is hydrogen or a protecting group such as —$CCH_3(OCH_2CH_3)_2$, T is a group that can be converted to a —$NH_2$ group, and Y is hydrogen or a protecting group such as lower alkyl, which compound of formula VI may have been synthesized by a condensation reaction according to Scheme 2 employing an 2,3-epoxypropyl derivative, such as an appropriate N-protected 2,3-epoxypropylamine derivative or an epichlorohydrin derivative, in which $R_1$ and $R_3$ is as defined above in formula I, and a suitable protected phosphinic acid derivative activated by O-silylation, in which X and Y are as defined in formula VI, and a Lewis acid such as anhydrous $ZnCl_2$, Scheme 2

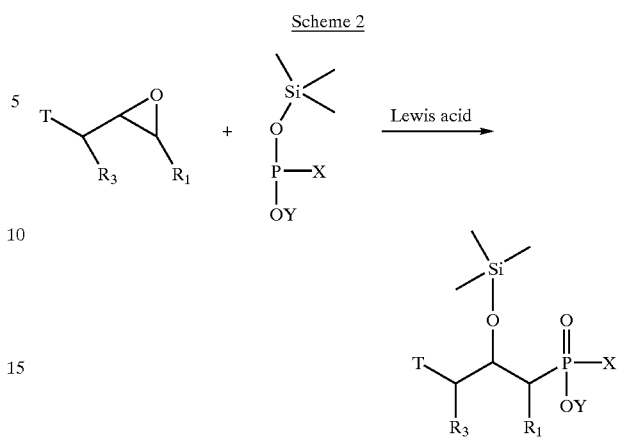

is a) converted by a reaction where the trimethylsilyl group is replaced by a hydrogen atom, a reaction where the T group as defined in formula VI is converted to —$NHR_4$ wherein $R_4$ is as defined above in formula I, and finally a hydrolytic reaction to obtain a compound of formula IV

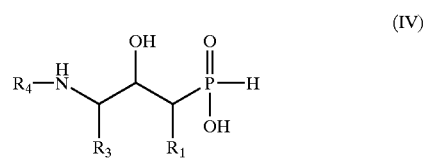
(IV)

wherein $R_1$, $R_3$ and $R_4$ are as defined above in formula I, and optionally convert the above resulting compound IV into another chemical compound of the formula IV and/or sepatate a resulting mixture of isomers into the individual isomers and/or convert a resulting salt into the free compound of the formula IV and/or into another salt and/or convert a resulting free compound of the formula IV into a salt to correspond to the above definition, or b) converted by a reaction where the trimethylsilyl group is replaced by hydrogen, an oxidative reaction, a reaction where the T group as defined in formula VI is converted to —$NHR_4$ wherein $R_4$ is as defined above in formula I, and finally a hydrolytic reaction to obtain a compound of formula III

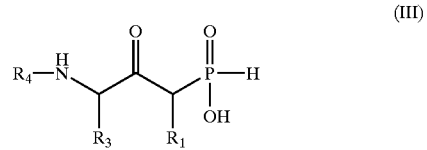
(III)

wherein $R_1$, $R_3$ and $R_4$ are as defined above in formula I, and optionally convert the above resulting compound III into another chemical compound of the formula III and/or sepatate a resulting mixture of isomers into the individual isomers and/or convert a resulting salt into the free compound of the formula III and/or into another salt and/or convert a resulting free compound of the formula III into a salt to correspond to the above definition, or c) converted by a reaction where the trimethylsilyl group is replaced by hydrogen, a deoxohalogenation reaction, a reaction where the T group as defined in formula VI is converted to —NHR$_4$ wherein R$_4$ is as defined above in formula I, and finally a hydrolytic reaction to obtain a compound of formula V

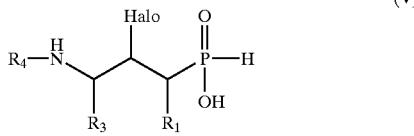

(V)

wherein R$_1$, R$_3$ and R$_4$ are as defined above in formula I, and Halo is a halogen atom, and optionally convert the above resulting compound V into another chemical compound of the formula V and/or sepatate a resulting mixture of isomers into the individual isomers and/or convert a resulting salt into the free compound of the formula V and/or into another salt and/or convert a resulting free compound of the formula V into a salt to correspond to the above definition; or C) A Compound of Formula VII

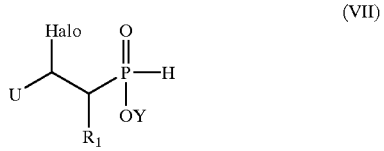

(VII)

in which R$_1$ is as defined above in formula I, X is hydrogen or a protecting group such as —CCH$_3$ (OCH$_2$CH$_3$)$_2$, U is an electron-withdrawing group, such as for instance —CN or —CO$_2$Et which can be converted to a —CH$_2$NH$_2$ group, and Y is hydrogen or a protecting group such as lower alkyl, and Halo is a halogen atom, which compound of formula VII may have been synthesized by an addition reaction according to Scheme 3 employing an unsaturated compound in which R$_1$ is as defined above in formula I, U and halo are as defined in formula VII, and a suitable protected phosphinic acid derivative activated by O-silylation, in which X and Y are as defined in formula VII, Scheme 3

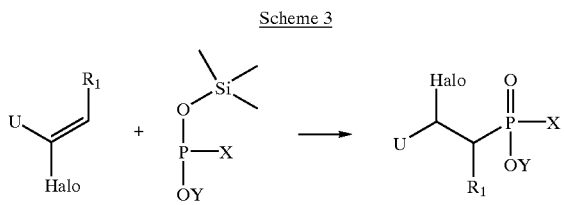

is converted by a reaction where the U group is being converted to —NHR$_4$ wherein R$_4$ is a defined above in formula I, and a hydrolytic reaction to obtain a compound of formula VIII

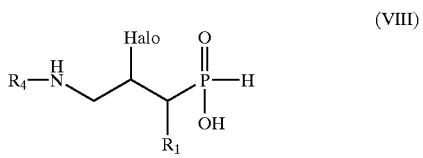

(VIII)

wherein R$_1$ and R$_4$ are as defined above in formula I and Halo is a halogen atom, and optionally convert the above resulting compound viii into another chemical compound of the formula VIII and/or separate a resulting mixture of isomers into the individual isomers and/or convert a resulting salt into the free compound of the formula VIII and/or into another salt and/or convert a resulting free compound of the formula VIII into a salt to correspond to the above definition; or D) A Compound of Formula IX Optionally as an Individual Stereo Isomer

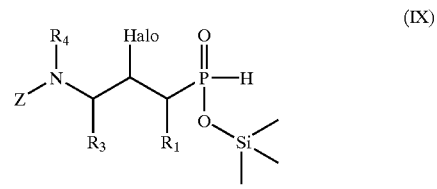

(IX)

in which R$_1$, R$_3$ and R$_4$ are as defined in formula I, Z is a protecting group such as t-butyloxycarbonyl and Halo is a halogen atom, which compound of formula IX may have been synthesized by a substitution reaction according to Scheme 4 employing an electrophilic compound in which R$_1$, R$_3$ and R$_4$ are as defined above, L is a leaving group such as iodo, Z and Halo are as defined above, and phosphinic acid activated by O-silylation, Scheme 4

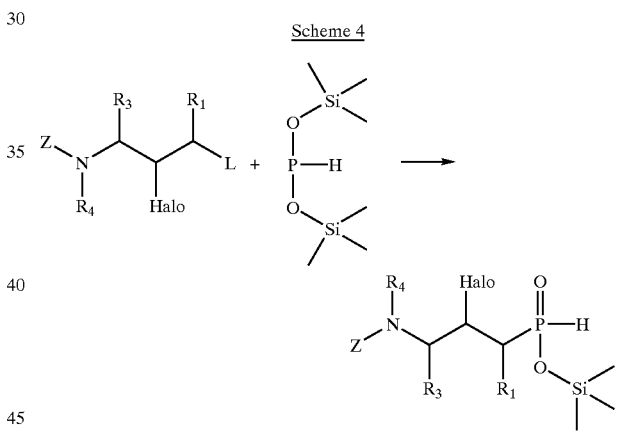

is converted by a hydrolytic reaction to a compound of formula V

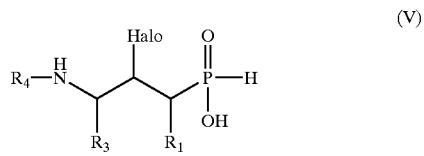

(V)

wherein R$_1$, R$_3$ and R$_4$ are as defined above in formula I, and optionally convert the above resulting compound V into another chemical compound of the formula V and/or sepatate a resulting mixture of isomers into the individual isomers and/or convert a resulting salt into the free compound of the formula V and/or into another salt and/or convert a resulting free compound of the formula V into a salt to correspond to the above definition; or E) A Compound of Formula XI

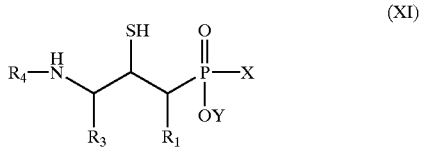
(XI)

in which $R_1$, $R_3$ and $R_4$ are as defined above in formula I, X is hydrogen or a protecting group such as —$CCH_3$($OCH_2CH_3)_2$, and Y is hydrogen or a protecting group such as lower alkyl, which compound of formula XI may have been synthesized by an addition reaction according to Scheme 4 treating an unsaturated phosphinic acid derivative, in which $R_1$, $R_3$ and $R_4$ are as defined in above in formula I, with $H_2S$, a mercaptide ion ($HS^-$) or a protected mercapto compound such as benzyl thiol in which case the protective group thereafter is removed Scheme 5

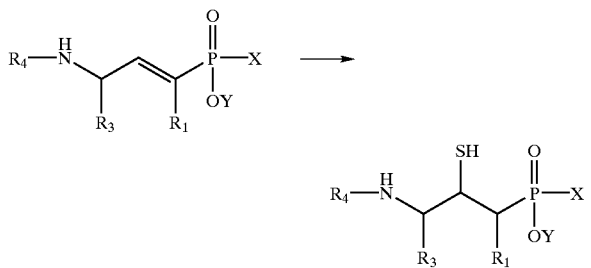

is converted by a hydrolytic reaction to obtain a compound of formula XII,

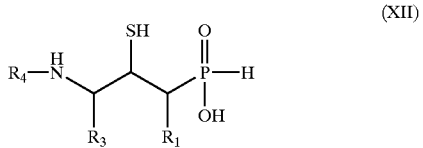
(XII)

in which $R_1$, $R_3$ and $R_4$ are as defined above in formula I, and optionally convert the above resulting compound XII into another chemical compound of the formula XII and/or sepatate a resulting mixture of isomers into the individual isomers and/or convert a resulting salt into the free compound of the formula XII and/or into another salt and/or convert a resulting free compound of the formula XII into a salt to correspond to the above definition.

DETAILED DESCRIPTION OF THE INVENTION

The invention is described more in detail by the following non-limiting examples

EXAMPLE 1

(3-Amino-2-fluoropropyl)phosphinic Acid

To an ice bath cooled solution of ethyl (3-amino-2-fluoro-3-oxopropyl)(diethoxymethyl)phosphinate in THF (tetrahydrofuran) was added 1 M $BH_3$-THF while under an argon atmosphere. After 10 minutes, the solution was heated to reflux for 2.5 h. The solution was cooled to room temperature and 6 N HCl (200 mL) was added. The THF was removed by rotoevaporation and the aqueous layer refluxed for 2.5 h. The solution was cooled and evaporated. The residue was purified by ion exchange column chromatography (DOWEX® 50WX-8-200, $H^+$ form, 3.5×4.0 cm). The ion exchange resin was pre-washed with 2:1 methanol/water (400 mL). The crude product dissolved in 1:1 methanol/water was loaded onto the column and washed with 1:1 methanol/water (400 mL). The eluent was changed to 3:1 methanol/concentrated ammonium hydroxide. Two fractions (150 mL totally) were combined and evaporated to give 645 mg (34%) of (3-amino-2-fluoropropyl)phosphinic acid as a white solid. Data: mp 203–207° C.; $R_f$=0.35 (60:40:1 methanol, methylene chloride, concentrated ammonium hydroxide); $^1$H NMR (300 MHz, $D_2O$) δ7.11 (d, J=528 Hz, 1H), 5.18 (dm, J=54 Hz, 1H), 3.28–3.45 (m, 2H), 1.65–2.23 (m, 2H); $^{13}$C NMR (125 MHz, $D_2O$+Dioxane) δ87.8 (d, J=170 Hz), 44.3 (dd, J=12.6, 21.6 Hz), 35.6 (dd, J=20.2, 86.5 Hz); APIMS: m/z=142 (M+H)$^+$.

EXAMPLE 2

(2S)-(3-Amino-2-hydroxypropyl)phosphinic Acid

A mixture of ethyl (2S)-(3-amino-2-hydroxypropyl)(1,1-diethoxyethyl)phosphinate (1.0 g, 3.5 mmol) and concentrated HCl (50 mL) was heated to reflux for 2 h. The solution was cooled to room temperature and evaporated. The residue was dissolved in methanol (100 ml) and treated with propylene oxide (2 ml) at room temperature. After the mixture was stirred for 5 hours, the precipitated solid was collected by decanting off the solvent. The solid was dried with a stream of argon to give 220 mg (45%) of (2S)-(3-amino-2-hydroxypropyl)phosphinic acid as a white solid. Data: $^1$H NMR (300 MHz, $D_2O$) δ7.1 (d, J=540 Hz, 1H), 4.2 (m, 1H), 2.9–3.2 (m, 2H), 1.7–2.0 (m, 2H); $^{31}$P NMR (121 MHz, $D_2O$) δ24.2 (d, J=522 Hz); FABMS: m/z=140 (M+H)$^+$; $[\alpha]_D$ at 20° C.=+8° (0.5% in 0.1M HCl).

EXAMPLE 3

(2R)-(3-Amino-2-hydroxypropyl)phosphinic Acid

A mixture of ethyl (2R)-(3-amino-2-hydroxypropyl)(1,1-diethoxyethyl)phosphinate (0.9 g, 3.2 mmol) and concentrated HCl (50 mL) was heated to reflux for 2 h. The solution was cooled to room temperature and evaporated. The residue was dissolved in methanol (50 ml) and treated with propylene oxide (3 ml) at room temperature. After the mixture was stirred for 5 hours, the precipitated solid was collected by decanting off the solvent. The solid was dried with a stream of argon to give 260 mg (59%) of (2R)-(3-amino-2-hydroxypropyl)phosphinic acid as a white solid. Data: $^1$H NMR (300 MHz, $D_2O$) δ7.1 (d, J=540 Hz, 1H), 4.2 (m, 1H), 2.9–3.2 (m, 2H), 1.7–2.0 (m, 2H); $^{31}$P NMR (121 MHz, $D_2O$) δ23.9 (d, J=525 Hz); FABMS: m/z=140 (M+H)$^+$; $[\alpha]_D$ at 20° C.=−8° (0.5% in 0.1M HCl).

EXAMPLE 4

(3-Amino-2-oxopropyl)phosphinic Acid

A sample of ethyl [3-[N-(tert-butoxycarbonyl)amino]-2-oxopropyl](1,1-diethoxyethyl)phosphinate (8.11 g, 21.0 mmol) was dissolved in 3 N HCl (400 mL) which was previously deoxygenated by bubbling $N_2$ through the solution. The mixture was stirred for 14 h at room temperature and then concentrated. The residue was coevaporated with methanol. The residue was then dissolved in methanol (10 mL) and propylene oxide was added (10 mL). The mixture was stirred for 6 h and the resulting precipitate isolated by filtration. The solid was washed with cold methanol and dried under vacuum at 50° C. to give 2.1 g (73%) of (3-amino-2-oxopropyl)phosphinic acid as an off-white solid. Data: mp 126–127° C.; $R_f$=0.64 (85:15 methanol, water); $^1$H NMR (300 MHz, $D_2O$) δ7.13 (d, J=551 Hz, 1H), 4.14 (s, 2H), 3.14 (d, J=18 Hz, 2H); $^{13}$C NMR (75 MHz, $D_2O$+Dioxane) δ199.5, 49.2, 47.3 (d, J=69 Hz); FABMS: m/z=138 (M+H)$^+$.

EXAMPLE 5

(2R)-(3-Amino-2-fluoropropyl)phosphinic Acid

Ammonium hypophosphite (73.8 g, 0.89 mol) was added to 3 necked 2-L flask equipped with a mechanical stirrer, thermometer, addition funnel and an argon bubbler. The flask was placed in a water bath at room temperature and N,O-Bis-(trimethylsilyl)acetamide (215 mL, 0.87 mol-BSA) was added at such a rate that the internal temperature was maintained below 38° C. (30 minutes approx.) using ice cooling. Upon completing the addition of BSA, the reaction mixture was heated to 45–48° C. and maintained at this temperature for 1 h. The reaction was cooled to room temperature and a solution of tert-butyl (2R)-2-fluoro-3-iodopropylcarbamate (27.3 g, 0.09 mol) in methylene chloride (300 mL) was added to the reaction mixture. The reaction was then allowed to stir at room temperature for 18 h. The reaction mixture was cooled to 0° C. and was cautiously quenched with methanol (275 mL) and then with water (32 mL). The reaction mixture was stirred for 30 min after which the reaction was filtered and the solids were washed with methanol. The filtrate was concentrated and the residue placed under high vacuum (0.1 mm Hg) overnight. The crude residue was triturated with methylene chloride, methanol, concentrated ammonium hydroxide solution (80:20:1) and was filtered. The filtrate was concentrated under reduced pressure and the trituration was repeated. The crude concentrate was transferred to a 2-L flask, dissolved in methanol (375 mL) and placed in a water bath at room temperature. A saturated solution of hydrogen chloride gas in ethyl acetate (500 mL) was added and the mixture stirred for 3 h. The reaction mixture was filtered and the solids were washed with a mixture of methanol and ethyl acetate (90:10). The filtrate was concentrated under reduced pressure and the crude product was passed through a Dowex® 50WX8-200 mesh H$^+$ form (500 g, 8×15 cm) column eluting with 1:1 methanol/water until no further material was detected by TLC analysis. The requisite crude product was then eluted with 1:3 concentrated ammonium hydroxide solution/methanol. The product was further purified by column chromatography eluting with chloroform, methanol, concentrated ammonium hydroxide solution (6:3:1) to afford (2R)-(3-amino-2-fluoropropyl)phosphinic acid as a white solid (3.12 g, 24%).

$^1$H NMR (300 MHz, $D_2O$) δ7.90 (s, 0.5H), 6.15 (s, 0.5H), 5.12–5.29 (m, 0.5H), 4.92–5.10 (m, 0.5H), 3.12–3.42 (m, 2H), 1.74–2.26 (m, 2H).

EXAMPLE 6

(2S)-(3-Amino-2-fluoropropyl)phosphinic Acid

Ammonium hypophosphite (58.1 g, 0.70 mol) was added to a 3 necked 2-L flask equipped with a mechanical stirrer, thermometer, addition funnel and an argon bubbler. N,O-Bis-(trimethylsilyl)acetamide (175.9 mL, 0.71 mol-BSA) was added at such a rate that the internal temperature was maintained between 35–40° C. Upon completing the addition of BSA, the reaction mixture was maintained at 35–40° C. for 45 min. Methylene chloride (150 mL) was added and the mixture was stirred at 35–40° C. for an additional 45 min. The reaction was cooled to room temperature and a solution of tert-butyl (2S)-2-fluoro-3-iodopropylcarbamate (42.5 g, 0.14 mol) in methylene chloride (300 mL) was added to the reaction mixture. The reaction was then allowed to stir at room temperature overnight. The reaction mixture was cooled to 0° C. and was cautiously quenched with methanol (150 mL) and then with water (60 mL). The reaction was concentrated and the residue placed under high vacuum (0.1 mm Hg). The residue was adjusted to approximately pH 8 by the addition of concentrated ammonium hydroxide (50 mL) then methylene chloride (400 mL) and methanol (250 mL) were added. The resulting solids were filtered and the filtrate was concentrated. The residue was triturated with methylene chloride, methanol, concentrated ammonium hydroxide solution (80:20:1; 400 mL) and was filtered. The filtrate was concentrated under reduced pressure and the crude concentrate was dissolved in methanol (400 mL). A saturated solution of hydrogen chloride gas in ethyl acetate (600 mL) was added and the mixture stirred for 3 h. The reaction mixture was filtered and the filtrate was concentrated under reduced pressure. The crude product was passed through a Dowex® 50WX8–200 mesh H$^+$ form (450 g) column eluting with 1:1 methanol/water until no further material was detected by TLC analysis. The requisite crude product was then eluted with 1:3 concentrated ammonium hydroxide solution/methanol. The product was further purified by column chromatography eluting with methylene chloride, methanol, concentrated ammonium hydroxide solution (6:3:1) to afford (2S)-(3-amino-2-fluoropropyl)phosphinic acid as a white solid (3.46 g, 17%). $^1$H NMR (300 MHz, $D_2O$) δ7.90 (s, 0.5H), 6.15 (s, 0.5H), 5.12–5.29 (m, 0.5H), 4.92–5.10 (m, 0.5H), 3.12–3.42 (m, 2H), 1.74–2.

EXAMPLE 7

(3-Amino-1-fluoro-2-hydroxypropyl)phosphinic Acid

Ethyl (3-(N-(tert-butoxycarbonyl)amino)-1-fluoro-2-hydroxypropyl)(1,1-diethoxyethyl)phosphinate (180 mg, 4.5 mmol) was dissolved in methanol (2 mL), treated with 3 N Hydrochloric acid (20 mL, 60.0 mmol, sparged with argon immediately prior to use). The mixture was stirred at room temperature for 6 hours under an argon atmosphere. The reaction mixture was concentrated under reduced pressure, the crude product was re-dissolved in methanol (5 mL); the residual water removed by co-evaporation under reduced pressure with methanol. The crude product (70 mg) was purified by column chromatography (1×10 cm column) eluting with methylene chloride, methanol, concentrated ammonium hydroxide (6:3:1). The fractions containing product were concentrated under reduced pressure, co-evaporated with acetonitrile (2×10 ml) then with methanol (1×10 mL) and dried overnight under high vacuum (0.1 mm Hg). This procedure afforded (3-amino-1-fluoro-2-hydroxypropyl)phosphinic acid as a white solid (40 mg, 56%). $^1$H NMR (300 MHz, $D_2O$) δ7.93 (s, 0.5H), 6.11 (s, 0.5H), 4.60–4.20 (m, 2H), 3.42–3.08 (m, 2H).

EXAMPLE 8

(3-Amino-2-fluoro-1-methylpropyl)phosphinic Acid

To an ice bath cooled solution of ethyl 3-amino-2-fluoro-1-methyl-3-oxopropyl(diethoxymethyl)phosphinate (1.6 g, 5.3 mmol) in THF (15 ml) was added 1 M BH$_3$-THF (12.3 mL, 12.3 mmol) while under an argon atmosphere. After 10 minutes, the solution was heated to reflux for 3 h. The solution was cooled to room temperature and 6 N HCl (100 mL) was added dropwise. The THF was removed by rotovap and another portion of 6 N HCl (100 mL) was added. The mixture was refluxed for 3 h. The solution was cooled, evaporated, co-evaporated with water and then with etanol. The residue was purified ion exchange chromatography (DOWEX® 50WX-8-200, H$^+$ form, 3.5×4.0 cm). The ion exchange resin was prewashed with 2:1 methanol/water. The crude product dissolved in 1:1 methanol/water was loaded onto the column and washed with 1:1 methanol/water. The eluent was changed to 3:1 methanol/concentrated ammonium hydroxide. The appropriate fractions were combined and evaporated to give 150 mg (15%) of a diastereomeric mixture of (3-amino-2-fluoro-1-methylpropyl)phosphinic acid as an oil. Data: $^1$H NMR (400 MHz, D$_2$O) δ6.2–7.8 (m, 1H), 4.8–5.2 (m, 1H), 3.2–3.5 (m, 2H), 1.8–2.2 (m, 1H), 1.0–1.2 (m, 3H); MS: m/z=156 (M+H)$^+$.

The following intermediates were used in the preparation of compounds of the invention.

INTERMEDIATES

EXAMPLE I1

Ethyl 3-[(diethoxymethyl)(ethoxy)phosphoryl]-2-fluoropropanoate

Intermediate to the Compound According to Example 1

A mixture of ethyl (diethoxymethyl)phosphinate (26.0 g, 133 mmol) and 1,1,1,3,3,3-hexamethyldisilazane (28 mL, 133 mmol) was heated to reflux for 2 h under an argon atmosphere. The mixture was cooled to room temperature and fluoroacrylate (10.5 g, 89.0 mmol) was added. The reagents were heated to 60° C. for three days under an argon atmosphere. The mixture was cooled to room temperature, diluted with ethyl acetate (300 mL), washed with 1 N HCl (2×150 mL) and saturated sodium chloride (100 mL). The organic layer was dried over MgSO$_4$, filtered, and evaporated to give 32.0 g of a yellow oil. The residue was purified by column chromatography on a wet-packed silica gel column (6×30 cm) eluting with 97:3 methylene chloride/methanol. The appropriate fractions were combined and evaporated to give 16.0 g (57%) of ethyl 3-[(diethoxymethyl)(ethoxy)phosphoryl]-2-fluoropropanoate as a clear oil. Data: $^1$H NMR (300 MHz, CDCl$_3$) δ5.32 (dm, 1H), 4.67–4.77 (m, 1H), 4.18–4.32 (m, 2H), 3.58–3.91 (m, 4H), 2.30–2.62 (m, 2H), 1.20–1.41 (m, 9H).

EXAMPLE I2

Ethyl (3-amino-2-fluoro-3-oxopropyl)(diethoxymethyl)phosphinate

Intermediate to Compound According to Example 1

To a solution of ethyl 3-[(diethoxymethyl)(ethoxy)phosphoryl]-2-fluoropropanoate (16.0 g, 51.1 mmol) in ethanol (22 mL) was added concentrated ammonium hydroxyde (14.8 N, 3.5 mL, 51.1 mmol). The solution was stirred for 16 h and evaporated. The residue was purified by chromatography on a wet-packed silica gel column (7×37 cm) eluting with 96.5:3.5 methylene chloride/methanol. The appropriate fractions were combined and evaporated to give 3.43 g (27%) of ethyl (3-amino-2-fluoro-3-oxopropyl)(diethoxymethyl)phosphinate as a clear oil. Data: $^1$H NMR (300 MHz, CDCl$_3$) δ6.43 (s, 1H), 5.70 (s, 1H), 5.21–5.49 (dm, 1H), 4.7 (dd, 1H), 4.18–4.31 (m, 2H), 3.65–3.91 (m, 4H), 2.21–2.81 (m, 2H), 1.30–1.40 (m, 3H), 1.20–1.28 (m, 6H).

EXAMPLE I3

Ethyl (2R)-(3-chloro-2-hydroxypropyl)(1,1-diethoxyethyl)phosphinate (Intermediate to the Compound According to Example 2)

After a mixture of ethyl (diethoxyethyl)phosphinate (15.0 g, 71 mmol) and toluene was evaporated to dryness, the residue and 1,1,1,3,3,3-hexamethyldisilazane (13.2 g, 82 mmol) was heated to reflux for 3 h under an argon atmosphere. The mixture was cooled to room temperature and evaporated. (R)-Epichlorohydrin (6.6 g, 71 mmol) and anhydrous zinc chloride (2.5 g, 18 mmol) were added and the reagents were heated to 60° C. over night under an argon atmosphere. The mixture was cooled to room temperature, diluted with methylene chloride and water. The organic layer was washed with water, dried over MgSO$_4$, filtered, and evaporated to give 20.7 g of a yellow oil. The residue was dissolved in methanol (150 mL) containing 1% acetic acid and the solution was stirred over night. The solvent was removed to give 17.7 g (82%) of ethyl (2R)-(3-chloro-2-hydroxypropyl)(1,1-diethoxyethyl)phosphinate as a clear oil. Data: $^1$H NMR (500 MHz, CDCl$_3$) δ4.3–4.4 (m, 1H), 4.1–4.3 (m, 2H), 3.5–3.8 (m, 4H), 1.9–2.4 (m, 2H), 1.5 (dd, J=2.3, 11.4 Hz, 3H), 1.32–1.37 (m, 3H), 1.18–1.24 (m, 6H).

EXAMPLE I4

Ethyl (2S)-(3-amino-2-hydroxypropyl)(1,1-diethoxyethyl)phosphinate

Intermediate to the Compound According to Example 2

A solution of ethyl (2R)-(3-chloro-2-hydroxypropyl)(1,1-diethoxyethyl)phosphinate (5.0 g, 17 mmol) in ethanol containing 9% of ammonia was stirred in an autoclave at room temperature for 4 days and at 60° C. for one further day. The solution was evaporated and the residue was purified by chromatography on a wet-packed silica gel column eluting with methylene chloride/methanol (5–8% MeOH) containing 5% triethylamine. The appropriate fractions were combined, evaporated and diluted with methylene chloride and water. The aqueous layer was pH adjusted by the addition of a few mL of 10% aqueous Na$_2$CO$_3$ and repeatedly extracted with methylene chloride. The combined organic layers were dried over Na$_2$SO$_4$ and evaporated to give 1.2 g (26%) of ethyl (2S)-(3-amino-2-hydroxypropyl)(1,1-diethoxyethyl)phosphinate as a clear oil. Data: $^1$H NMR (300 MHz, CDCl$_3$) δ4.40–4.55 (b, 1H), 4.10–4.30 (m, 2H), 3.55–3.80 (m, 4H), 3.20–3.30 (m, 1H), 3.00–3.10 (m, 1H), 2.00–2.40 (m, 2H), 1.45–1.53 (dd, J=3.4, 11.7 Hz, 3H), 1.30–1.40 (m, 3H), 1.15–1.25 (m, 6H).

EXAMPLE I5

Ethyl (2S)-(3-chloro-2-hydroxypropyl)(1,1-diethoxyethyl)phosphinate

Intermediate to the Compound According to Example 3

After a mixture of ethyl (diethoxyethyl)phosphinate (15.0 g, 71 mmol) and toluene was evaporated to dryness, the residue and 1,1,1,3,3,3-hexamethyldisilazane (13.2 g, 82 mmol) was heated to reflux for 3 h under an argon atmosphere. The mixture was cooled to room temperature and evaporated. (S)-Epichlorohydrin (6.6 g, 71 mmol) and anhydrous zinc chloride (2.5 g, 18 mmol) were added and the reagents were heated to 60° C. over night under an argon atmosphere. The mixture was cooled to room temperature, diluted with methylene chloride and water. The organic layer was washed with water, dried over $MgSO_4$, filtered, and evaporated to give 20.7 g of a yellow oil. The residue was dissolved in methanol (150 mL) containing 1% acetic acid and the solution was stirred over night. The solvent was removed to give 16.8 g (79%) of ethyl (2S)-(3-chloro-2-hydroxypropyl)(1,1-diethoxyethyl)phosphinate as a clear oil. Data: $^1$H NMR (500 MHz, $CDCl_3$) δ4.4 (m, 1H), 4.2–4.3 (m, 2H), 3.6–3.8 (m, 4H), 1.9–2.4 (m, 2H), 1.5 (dd, J=2.3, 11.4 Hz, 3H), 1.32–1.37 (m, 3H), 1.18–1.24 (m, 6H).

EXAMPLE I6

Ethyl (2R)-(3-amino-2-hydroxypropyl)(1,1-diethoxyethyl)phosphinate

Intermediate to the Compound According to Example 3

A solution of ethyl (2S)-(3-chloro-2-hydroxypropyl)(1,1-diethoxyethyl)phosphinate (5.0 g, 17 mmol) in ethanol containing 9% of ammonia was stirred in an autoclave at room temperature for 6 days and at 55° C. for one further day. The solution was evaporated and the residue was purified by chromatography on a wet-packed silica gel column eluting with methylene chloride/methanol (5–8% MeOH) containing 5% triethylamine. The appropriate fractions were combined, evaporated and diluted with methylene chloride and water. The aqueous layer was pH adjusted by the addition of a few mL of 10% aqueous $Na_2CO_3$ and repeatedly extracted with methylene chloride. The combined organic layers were dried over $Na_2SO_4$ and evaporated to give 0.9 g (19%) of ethyl (2R)-(3-amino-2-hydroxypropyl)(1,1-diethoxyethyl)phosphinate as a clear oil. Data: $^1$H NMR (500 MHz, $CDCl_3$) δ4.1–4.3 (m, 2H), 4.05 (b, 1H), 3.60–3.80 (m, 4H), 2.4–2.9 (m, 2H), 1.7–2.1 (m, 2H), 1.4–1.5 (dd, 3H), 1.3–1.4 (m, 3H), 1.2 (m, 6H).

EXAMPLE I7

Ethyl [b 3-[N-(tert-butoxycarbonyl)amino]-2-oxopropyl](1,1-diethoxyethyl)phosphinate Intermediate to the Compound According to Example 4

To a solution of diisopropylamine (3.0 mL, 21 mmol) in THF (5 mL) at −10° C. was added dropwise n-BuLi (2.5 M in hexanes, 8.6 mL, 21 mmol). After 10 minutes, the reaction was cooled to −78° C. and a solution ethyl (1,1-diethoxyethyl)(methyl)phosphinate (4.80 g, 21.0 mmol) in THF (5 mL) was added dropwise. After the addition, the solution was stirred at −78° C. for 1 h. A solution of N-Boc-glycine methyl ester (810 mg, 4.3 mmol) in THF (15 mL) was added dropwise. After the addition was complete, the reaction mixture was stirred for 45 minutes. Acetic acid (1.2 mL, 21 mmol) was added and the reaction mixture was warmed to room temperature. The reaction mixture was partitioned between methylene chloride and water and the layers were separated. The aqueous layer was extracted once with methylene chloride. The combined organic extracts were dried over $MgSO_4$, filtered, and evaporated to give 4.89 g of an oil. The residue was purified by chromatography on 100 g of silica gel eluting with ethyl acetate. The appropriate fractions were collected to give 1.2 g (74%) of ethyl [3-[N-(tert-butoxycarbonyl)amino]-2-oxopropyl](1,1-diethoxyethyl)phosphinate as an oil. Data: $^1$H NMR (300 MHz, $CDCl_3$) δ5.48 (s, 1H), 4.10–4.30 (m, 2H), 4.17 (d, 2H), 3.60–3.80 (m, 4H), 3.01–3.30 (m, 2H), 1.52 (d, 3H), 1.43 (s, 9H), 1.32 (t, 3H), 1.19 (t, 6H).

EXAMPLE I8

(2R)-3-(Dibenzylamino)-2-fluoro-1-propanol

Intermediate to the Compound According to the Example 5

Lithium borohydride (5.3 g, 0.24 mol) was suspended in THF (200 mL) under a nitrogen atmosphere and cooled to −15° C. with stirring. Methyl (2R)-3-(dibenzylamino)-2-fluoropropanoate (56.6 g, 0.19 mol) was suspended in THF (250 mL) and added dropwise to the mixture over 1 h; the internal temperature was maintained below −10° C. during the addition. On completion of addition, the reaction mixture was allowed to warm to room temperature and stirred at this temperature for 17 h. The reaction mixture was cooled to 0° C. and cautiously quenched with a saturated aqueous solution of ammonium chloride (300 mL). The reaction mixture was extracted with ethyl acetate (2×200 mL) and the organic phase was concentrated under reduced pressure. The crude residue was dissolved in 2 N hydrochloric acid (200 mL, pH=2 approx.) and the aqueous phase was washed with ether (2×200 mL). The aqueous phase was basified (pH=10 approx.) with 80% ammonium hydroxide in brine, extracted with ethyl acetate (3×200 mL), dried over anhydrous sodium sulfate (10 g), filtered and concentrated under reduced pressure to afford (2R)-3-(dibenzylamino)-2-fluoro-1-propanol (48 g, 93%) as a yellow oil.

$^1$H NMR (300 MHz, $CDCl_3$) δ7.15–7.38 (m, 10H), 4.65–4.78 (m, 0.5H), 4.48–4.58 (m, 0.5H), 3.50–3.82 (m, 6H), 2.70–2.88 (m, 2H).

EXAMPLE I9

(2R)-3-Amino-2-fluoro-1-propanol

Intermediate to the Compound According to the Example 5

(2R)-3-(dibenzylamino)-2-fluoro-1-propanol (29.2 g, 0.11 mol) was dissolved in ethanol (300 mL). Ten wt. % Palladium (II) hydroxide on carbon (5.0 g) was added and the mixture placed on a Parr® shaker and shaken under a hydrogen atmosphere (55 psi) for 6 h. When no further hydrogen uptake was observed, the mixture was filtered through a pad of Celite® (20 g). A fresh batch of palladium (II) hydroxide (5 g) was added to the ethanol mixture and re-subjected to the hydrogenation conditions described above for 17 h. The crude reaction mixture was filtered through Celite® and concentrated under reduced pressure to afford (2R)-3-amino-2-fluoro-1-propanol as a pale yellow oil (9.6 g, 96%).

$^1$H NMR (300 MHz, $CD_3OD$) δ4.78–5.00 (br s, 3H), 4.49–4.62 (m, 0.5H), 4.32–4.46 (m, 0.5H), 3.54–3.70 (m, 2H), 2.70–2.96 (m, 2H).

EXAMPLE I10

Tert-butyl (2R)-2-fluoro-3-hydroxypropylcarbamate

Intermediate to the Compound According to the Example 5

(2R)-3-amino-2-fluoro-1-propanol (4.6 g, 49 mmol) was dissolved in 25% aqueous dioxane (160 mL), potassium carbonate (7.1 g, 51 mmol) was added and the mixture cooled to 0° C. Di-tert-butyl dicarbonate (11.6 g, 53 mmol) was added in two portions. The mixture was then allowed to warm to room temperature overnight. The crude reaction mixture was concentrated to dryness, water (150 mL) was added followed by saturated aqueous potassium hydrogen sulfate (until pH=3 approx.). The organic material was extracted with methylene chloride (2×150 mL), dried over sodium sulfate, filtered and concentrated under reduced pressure to afford tert-butyl (2R)-2-fluoro-3-hydroxypropylcarbamate (9.5 g, 100%) as a colorless oil.

$^1$H NMR (300 MHz, CDCl$_3$) δ4.82–5.04 (br s, 1H), 4.62–4.72 (m, 0.5H), 4.48–4.58 (m, 0.5H), 3.62–3.72 (m, 2H), 3.32–3.62 (m, 2H), 3.20–3.44 (br s, 1H), 1.48 (s, 9H).

EXAMPLE I11

Tert-butyl (2R)-2-fluoro-3-iodopropylcarbamate

Intermediate to the Compound According to the Example 5)

Imidazole (26.6 g, 0.39 mol) was dissolved in methylene chloride (400 mL) at room temperature. Iodine (102.5 g, 0.39 mol) was added and the reaction mixture was stirred for 10 min at room temperature and then cooled to 0° C. Triphenylphosphine (102.5 g, 0.39 mol) was added portionwise over 10 min such that the internal temperature remained below 10° C. A solution of tert-butyl (2R)-2-fluoro-3-hydroxypropylcarbamate (60.4 g, 0.31 mol) in methylene chloride (100 mL) was added dropwise. On completion of addition of tert-butyl (2R)-2-fluoro-3-hydroxypropylcarbamate, additional methylene chloride (200 mL) was added. The reaction mixture was allowed to warm to room temperature and stirring was continued for 17 h. The reaction mixture was filtered through a pad of Celite® (50 g) and washed with additional methylene chloride. The filtrate was concentrated under reduced pressure and purified by silica gel column chromatography eluting with methylene chloride. This procedure afforded tert-butyl (2R)-2-fluoro-3-iodopropylcarbamate as a white solid (64.7 g, 68%).

$^1$H NMR (300 MHz, CDCl$_3$) δ4.80–5.10 (br s, 1H), 4.58–4.72 (m, 0.5H), 4.42–4.56 (m, 0.5H), 3.48–3.70 (m, 1H), 3.20–3.46 (m, 3H), 1.48 (s, 9H).

EXAMPLE I12

Methyl (2S)-3-(dibenzylamino)-2-fluoropropanoate

Intermediate to the Compound According to the Example 6

Methyl (2R)-2-(dibenzylamino)-3-hydroxypropanoate (231.7 g, 0.77 mol) was dissolved in THF (850 mL) and a solution of DAST (196 g, 1.2 mol) in THF (400 mL) was added slowly dropwise. Once the addition was complete, the reaction was stirred for an additional 1.5 h. TLC analysis indicated consumption of starting material. The reaction was then cooled to 0° C. and was quenched by the slow addition of water (1.5 l) followed by neutralization by the addition of solid sodium bicarbonate. Once neutral, a 1:1 mixture of concentrated ammonium hydroxide/saturated sodium chloride solution was added and the reaction was extracted with ethyl acetate and concentrated under reduced pressure. The crude mixture was purified by silica gel column chromatography eluting with ethyl acetate, hexanes (1:4) to provide the desired compound (188.3 g, 62%) as an oil.

$^1$H NMR (300 MHz, CDCl$_3$) δ7.18–7.38 (m, 10H), 5.12–5.17 (m, 0.5H), 4.95–5.00 (m, 0.5H), 3.81–3.87 (m, 2H), 3.69 (s, 3H), 3.49–3.55 (m, 2H), 2.90–3.12 (m, 2H).

EXAMPLE I13

(2S)-3-(Dibenzylamino)-2-fluoro-1-propanol

Intermediate to the Compound According to the Example 6

Lithium borohydride (17.7 g, 0.81 mol) was suspended in THF (400 mL) under a nitrogen atmosphere and cooled to −15° C. with stirring. Methyl (2S)-3-(dibenzylamino)-2-fluoropropanoate (188.3 g, 0.62 mol) was suspended in THF (400 mL) and added dropwise to the mixture. On completion of addition, the reaction mixture was allowed to warm to room temperature and stirred at this temperature for 3 h. TLC analysis indicated complete consumption of starting material. The reaction mixture was cooled to 0° C. and cautiously quenched with a saturated aqueous solution of ammonium chloride (300 mL). Additional water (400 mL) was added then the reaction mixture was extracted with ethyl acetate and the organic phase was concentrated under reduced pressure. The crude residue was dissolved in 2 N hydrochloric acid and the aqueous phase was washed twice with ether. The aqueous phase was basified (pH=10 approx.) with 80% ammonium hydroxide in brine, extracted with ethyl acetate, dried over anhydrous sodium sulfate, filtered and concentrated under reduced pressure to afford (2S)-3-(dibenzylamino)-2-fluoro-1-propanol (156.6 g, 92%) as a yellow oil. $^1$H NMR (300 MHz, CDCl$_3$) δ7.15–7.38 (m, 10H), 4.65–4.78 (m, 0.5H), 4.48–4.58 (m, 0.5H), 3.50–3.82 (m, 6H), 2.70–2.88 (m, 2H).

EXAMPLE I14

(2S)-3-Amino-2-fluoro-1-propanol

Intermediate to the Compound According to the Example 6

(2S)-3-(dibenzylamino)-2-fluoro-1-propanol (39.1 g, 0.14 mol) was dissolved in ethanol (300 mL). Ten wt. % Palladium (II) hydroxide on carbon (5.0 g) was added and the mixture placed on a Parr® shaker and shaken under a hydrogen atmosphere (55 psi) overnight. When no further hydrogen uptake was observed, the mixture was filtered through a pad of Celite®. A fresh batch of palladium (II) hydroxide (5 g) was added to the ethanol mixture and re-subjected to the hydrogenation conditions described above for 12 h. Again, when no further hydrogen uptake was observed, the mixture was filtered through a pad of Celite®. A fresh batch of palladium (II) hydroxide (5 g) was added to the ethanol mixture and re-subjected to the hydrogenation conditions described above for 12 h. The crude reaction mixture was filtered through Celite® and concentrated under reduced pressure to afford (2S)-3-amino-2-fluoro-1-propanol as a pale yellow oil (13.3 g, 100%). $^1$H NMR (300 MHz, CD$_3$OD) δ4.78–5.00 (br s, 3H), 4.49–4.62 (m, 0.5H), 4.32–4.46 (m, 0.5H), 3.54–3.70 (m, 2H), 2.70–2.96 (m, 2H).

EXAMPLE I15

Tert-butyl (2S)-2-fluoro-3-hydroxypropylcarbamate

Intermediate to the Compound According to the Example 6

(2S)-3-amino-2-fluoro-1-propanol (38.6 g, 0.41 mol) was dissolved in 25% aqueous dioxane (1.4 L), potassium carbonate (60.1 g, 0.43 mol) was added followed by di-tert-butyl dicarbonate (99.5 g, 0.46 mol). The mixture was stirred overnight. TLC analysis indicated complete consumption of starting material. The crude reaction mixture was concentrated to dryness, water (300 mL) was added followed by saturated aqueous potassium hydrogen sulfate (until pH=3 approx.). The organic material was extracted twice with methylene chloride, dried over sodium sulfate, filtered and concentrated under reduced pressure to afford tert-butyl (2S)-2-fluoro-3-hydroxypropylcarbamate (79.5 g, 99%) as a pale yellow oil. $^1$H NMR (300 MHz, CDCl$_3$) δ4.82–5.04 (br s, 1H), 4.62–4.72 (m, 0.5H), 4.48–4.58 (m, 0.5H), 3.62–3.72 (m, 2H), 3.32–3.62 (m, 2H), 3.20–3.44 (br s, 1H), 1.48 (s, 9H).

EXAMPLE I16

Tert-butyl (2S)-2-fluoro-3-iodopropylcarbamate

Intermediate to the Compound According to the Example 6

Imidazole (19.8 g, 0.29 mol) was dissolved in methylene chloride (900 mL) at room temperature. Iodine (73.9 g, 0.29 mol) was added and the reaction mixture was stirred for 10 min at room temperature and then cooled to 0° C. Triphenylphosphine (76.3 g, 0.29 mol) was added portionwise over 10 min such that the internal temperature remained below 10° C. A solution of tert-butyl (2S)-2-fluoro-3-hydroxypropylcarbamate (45.0 g, 0.23 mol) in methylene chloride (300 mL) was added dropwise. The reaction mixture was allowed to warm to room temperature and stirring was continued for 12 h. The reaction mixture was filtered through a pad of Celite® and washed with additional methylene chloride. The filtrate was concentrated under reduced pressure and purified by silica gel column chromatography eluting with methylene chloride. This procedure afforded tert-butyl (2S)-2-fluoro-3-iodopropylcarbamate as a colorless oil (42.5 g, 62%). $^1$H NMR (300 MHz, CDCl$_3$) δ4.80–5.10 (br s, 1H), 4.58–4.72 (m, 0.5H), 4.42–4.56 (m, 0.5H), 3.48–3.70 (m, 1H), 3.20–3.46 (m, 3H), 1.48 (s, 9H).

EXAMPLE I17

Ethyl (fluoromethyl)(1,1-diethoxyethyl)phosphinate

Intermediate to the Compound According to the Example 7

Sodium hydride (1.4 g, 57.1 mmol) was suspended in THF (50 mL) in a pressure flask under a nitrogen atmosphere and cooled to −10° C. with stirring. Ethyl (1,1-diethoxyethyl)phosphinate (10.0 g, 47.6 mmol) in THF (20 mL) was added dropwise to the mixture over 10 minutes; the internal temperature was maintained below 0° C. during the addition. On completion of addition, the reaction mixture was allowed to stir at this temperature for 90 minutes. The flask was cooled to −78° C. and chlorofluoromethane gas (9.7 g, 142.8 mmol) was condensed into the reaction mixture. The septum was removed and the flask was sealed with a screw thread stopper. The flask was then allowed to warm to room temperature and then heated at 50° C. for 24 h. The reaction mixture was cooled to 0° C. and cautiously quenched with water (25 mL). Methylene chloride (50 mL) was added to the reaction mixture and the emulsion was filtered through a pad of Celite® (20 g). The aqueous phase was extracted with methylene chloride (2×100 mL), dried over anhydrous magnesium sulfate, and the organic phase was concentrated under reduced pressure affording the crude product as a pale yellow oil (6.93 g). The crude residue was purified by silica gel column chromatography (6×25 cm column) eluting with 20% acetone in hexanes. This procedure afforded ethyl (fluoromethyl)(1,1-diethoxyethyl) phosphinate as a clear, colorless oil (4.4 g, 42%). $^1$H NMR (300 MHz, CDCl$_3$) δ4.94–4.54 (m, 2H), 4.32–4.20 (m, 2H), 3.82–3.54 (m, 4H), 1.60–1.44 (m, 3H), 1.40–1.28 (m, 3H), 1.26–1.08 (m, 6H).

EXAMPLE I18

Ethyl (3-(N-(tert-butoxycarbonyl)amino)-1-fluoro-2-oxopropyl)(1,1-diethoxyethyl)phosphinate Intermediate to the Compound According to the Example 7

To a solution of diisopropylamine (2.5 mL, 14.5 mmol, 3.5 eq) in THF (30 mL) at −10° C. was added dropwise (about 10 minutes) n-BuLi (1.4 M in hexanes, 9.0 mL, 14.5 mmol). After 10 minutes, the reaction was cooled to −78° C., and a solution of ethyl (fluoromethyl)(1,1-diethoxyethyl) phosphinate (2.0 g, 8.26 mmol, 2 eq) in THF (10 mL) was added dropwise over 10 minutes. After the addition the reaction mixture was stirred at −78° C. for 1 h. A solution of N-Boc-glycine methyl ester (0.8 g, 4.1 mmol) in THF (10 mL) was added dropwise over 10 minutes such that the internal temperature was maintained below −70° C. After the addition was complete the reaction was stirred at −78° C. for 1 h. The reaction was quenched with acetic acid (1 mL, 14.5 mmol) and then warmed to room temperature. Saturated aqueous sodium chloride (75 mL) was added to the reaction and the organic phase separated. The aqueous phase was then extracted with ethyl acetate (2×75 mL). The combined organic phase was dried over anhydrous sodium sulfate and concentrated under reduced pressure affording the crude product as a pale yellow oil (2.69 g). The crude product was purified by column chromatography (2×35 cm column), eluting with 40% ethyl acetate in hexane. This method afforded ethyl (3-(N-(tert-butoxycarbonyl)amino)-1-fluoro-2-oxopropyl)(1,1-diethoxyethyl)phosphinate as a clear colorless oil (0.73 g, 44%). $^1$H NMR (300 MHz, CDCl$_3$) δ5.78–5.24 (m, 2H), 4.52–4.08 (m, 4H), 3.94–3.50 (m, 4H), 1.62–1.51 (m, 3H), 1.50–1.32 (m, 3H), 1.42 (s, 9H), 1.30–1.12 (m, 6H).

EXAMPLE I19

Ethyl (3-(N-(tert-butoxycarbonyl)amino)-1-fluoro-2-hydroxypropyl)(1,1-diethoxyethyl)phosphinate Intermediate to the Compound According to the Example 7

To solution of ethyl (3-(N-(tert-butoxycarbonyl)amino)-1-fluoro-2-oxopropyl)(1,1-diethoxyethyl)phosphinate (0.7 g, 1.8 mmol) in methanol (30 mL) at −5° C. under a nitrogen atmosphere was added sodium borohydride (76 mg, 2.0 mmol) in one portion. A slight exotherm occurred; however, the internal temperature was maintained below −2° C. The reaction mixture was stirred at 0° C. for 1 h. The reaction mixture was quenched with saturated aqueous sodium hydrogen carbonate (5 mL). The crude mixture was concentrated under reduced pressure. The crude residue was extracted with ethyl acetate (30 mL), washed with saturated aqueous sodium chloride solution (5 mL) and dried over anhydrous magnesium sulfate. Removal of solvent under reduced pressure afforded the crude product as a pale yellow oil (580 mg). Purification by column chromatography afforded 2 fractions, which appeared to be consistent with different diastereomers of ethyl (3-(N-(tert-butoxycarbonyl)

amino)-1-fluoro-2-hydroxypropyl)(1,1-diethoxyethyl) phosphinate. The less polar fraction appeared to be a 1:1 mixture of two diastereomers, (210 mg, 29%). Whereas the more polar fraction was predominantly one diastereomer as judged by $^1$H NMR analysis (190 mg, 26%). $^1$H NMR of the more polar compound (300 MHz, CDCl$_3$) δ5.32–5.04 (br s, 1H), 4.88–4.82 (m, 0.5H), 4.72–4.68 (m, 0.5H), 4.40–4.08 (m, 4H), 3.90–3.26 (m, 6H), 1.66–1.52 (m, 3H), 1.50–1.32 (m, 3H), 1.44 (s, 9H), 1.30–1.12 (m, 6H).

EXAMPLE I20

Ethyl 3-[(diethoxymethyl)(ethoxy)phosphoryl]-2-fluorobutanoate (Intermediate to the Compound According to Example 8

A mixture of ethyl (diethoxymethyl)phosphinate (21.7.0 g, 110 mmol) and 1,1,1,3,3,3-hexamethyldisilazane (23.3 mL, 110 mmol) was heated to reflux for 2 h under an argon atmosphere. The mixture was cooled to room temperature and a diastereomeric mixture ethyl 2-fluorobut-2-enoate (14.6 g, 110 mmol) was added. The reagents were heated to 80° C. for one day and 120° C. for 2 hours under an argon atmosphere. The mixture was cooled to room temperature and another portion of trimethylsilyl activated ethyl (diethoxymethyl)phosphinate was added (this had been prepared from ethyl (diethoxymethyl)phosphinate (21.7.0 g, 110 mmol) and 1,1,1,3,3,3-hexamethyldisilazane (23.3 mL, 110 mmol) in the same way as above). The mixture was heated to 100° C. for three days and still another portion of trimethylsilyl activated ethyl (diethoxymethyl)phosphinate was added. The mixture was heated to 100° C. for three days under an argon atmosphere, cooled to room temperature and then diluted with ethyl acetate (300 mL). The solution was washed with 1 N HCl (2×200 mL) and saturated sodium chloride. The organic layer was dried over MgSO$_4$, filtered, and evaporated to give 42.0 g of a yellow oil. The residue was purified by chromatography on a wet-packed silica gel column eluting with methylene chloride and then with 98:2 methylene chloride/methanol. The appropriate fractions were combined and evaporated to give 3.6 g (10%) of ethyl 3-[(diethoxymethyl)(ethoxy)phosphoryl]-2-fluorobutanoate as a clear oil. $^1$H NMR (400 MHz, CDCl$_3$) δ4.9–5.6 (m, 1H), 4.7–4.8 (m, 1H), 4.2–4.4 (m, 4H), 3.6–4.0 (m, 4H), 2.6–2.9 (m, 1H), 1.2–1.4 (m, 12H).

EXAMPLE I21

Ethyl 3-amino-2-fluoro-1-methyl-3-oxopropyl (diethoxymethyl)phosphinate

Intermediate to the Compound According to the Example 8

To a solution of ethyl 3-[(diethoxymethyl)(ethoxy) phosphoryl]-2-fluorobutanoate (1.8 g, 5.5 mmol) in ethanol (3 mL) was added concentrated ammonium hydroxide (14.8 M, 0.5 mL, 7.4 mmol). The solution was stirred for 24 h at 40° C. and then evaporated to give 1.6 g (97%) of a diastereomeric mixture of ethyl 3-amino-2-fluoro-1-methyl-3-oxopropyl(diethoxymethyl)phosphinate as a clear oil. $^1$H NMR (400 MHz, CDCl$_3$) δ5.7–6.7 (m, 2H), 4.9–5.5.6 (m, 1H), 4.7–4.8 (m, 1H), 4.1–4.4 (m, 2H), 3.8–4.0 (m, 4H), 2.8–3.0 (m, 1H), 1.2–1.4 (m, 12H).

Pharmaceutical Preparations

The compound according to formula I of the present invention can be used as an active ingredient in a pharmaceutical preparation for oral, rectal, epidural, intravenous, intramuscular, subcutanous, nasal administration and administration by infusion or for any other suitable route of administration. Preferably the way of administration is oral or by injection/infusion.

The pharmaceutical preparations contain a compound of the present invention in combination with one or more pharmaceutically acceptable ingredients. The finished dosage forms are manufactured by known pharmaceutical processes. Usually the amount of active compounds is between 0.1–95% by weight of the preparation, preferably between 0.2–20% by weight in preparations for parenteral use and preferably between 1–50% by weight in preparations for oral administration.

In the preparation of pharmaceutical preparations containing a compound of the present invention in the form of solid dosage units for oral administration, the compound selected may be mixed with solid pharmaceutically acceptable ingredients (among these for instance disintegrating agents and lubricating agents). The mixture is then processed into granules, tablets, capsules or sachets.

Dosage units for rectal administration may be prepared in the form of suppositories; in the form of a gelatine rectal capsule; in the form of a ready-made micro enema; or in the form of a dry micro enema formulation to be reconstituted in a suitable solvent just prior to administration.

Liquid preparations for oral administration may be prepared in the form of syrups or suspensions, or in the form of a dry mixture to be reconstituted with a suitable solvent prior to use.

Solutions for parenteral administration may be prepared as a solution of a compound of the invention in a pharmaceutically acceptable solvent and are dispensed into ampoules or vials. They may also be prepared as a dry preparation to by reconstituted with a suitable solvent extemporaneously before use.

The typical daily dose of the active compound will depend on various factors such as for example the individual requirement of each patient, the route of administration and the disease. In general, dosages will be in the range of 1 μg to 100 mg per day and kg body weight, preferably 10 μg to 20 mg per day and kg body weight.

Biological Studies

[$^3$H]GABA Radioligand Binding Assay

Rat synaptic membranes were prepared from the whole brain of Sprague Dawley male rats essentially as described previously (Zukin, et al. (1974) Proc. Natl. Ac ad. USA 71, 4802–4807). The [$^3$H]GABA competition assay, modified from Olpe et al ((1990) Eur. J. Pharmacol. 187, 27–38), was performed in 200 μl TCI (Tris Calcium Isoguvacine) buffer (50 mM Tris (tri(hydroxymethyl)aminomethane), pH 7.4, 2.5 MM CaCl$_2$ and 40 μM isoguvacine) containing 20 nM [$^3$H]GABA (specific activity: 3 Tera Becquerel (TBq)/ mmol), test compound or solvent and 80 μg synaptic membrane protein using 96-well plates. After incubation for 12–20 min at room temperature, incubations were terminated by rapid filtration through a glass fiber filter (Printed filtermat B filters, Wallac) which had been pretreated with 0.3% polyethyleneimine, using a 96-well plate cell harvester (Skatron or Tomtec). The filters were washed with buffer containing 50 mM Tris (tris(hydroxymethyl)aminomethane) and 2.5 mM CaCl$_2$, pH 7.4, at 4° C. and then dried at 55° C. MeltiLex B/HS scintillator sheet (Wallac) was melted onto the filter, and radioactivity was determined in a Microbeta scintillation counter (Wallac).

Results and Discussion

The compounds of the present invention were found to have high affinities and potencies for the $GABA_B$ receptor as revealed by low $IC_{50}$ and $EC_{50}$ in the binding and ileum assays, respectively. The compounds have also been found to reduce TLOSR when administered i.v. as well as p.o. in animal models. Contrary to what has been claimed in the literature for 3-aminopropylphosphinic acid derivatives having a P—H bond, we found that the compounds of the present invention have high metabolic stability in animal models. Moreover, CNS side-effects (as measured by reduction in body temperature in the mouse) were not observable or only seen at very high doses. Therefore, the difference between therapeutic dose (inhibition of TLOSR in the dog model) and dose causing side-effects (in the mouse model) was unexpectedly high.

What is claimed is:

1. A compound according to formula I

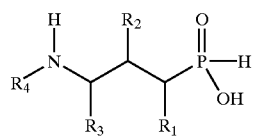

(I)

wherein
$R_1$ represents hydrogen;
$R_2$ represents hydroxy, fluoro or an oxo group;
$R_3$ represents hydrogen;
$R_4$ represents hydrogen;
or a stereoisomer thereof, or a pharmaceutically acceptable form of either selected from the group consisting of a salt, a solvate and a combination thereof, with the exception of the racemate of (3-amino-2-hydroxypropyl) phosphinic acid.

2. A according to claim 1 which is (3-amino-2-fluoropropyl)phosphinic acid or a stereoisomer thereof, or a pharmaceutically acceptable form of either selected from the group consisting of a salt, a solvate and a combination thereof.

3. A compound according to claim 2 which is (2R)-(3-amino-2-fluoropropyl)phosphinic acid or a pharmaceutically acceptable form thereof selected from the group consisting of a salt, a solvate and a combination thereof.

4. A compound according to claim 2 which is (2S)-(3-amino-2-fluoropropyl)phosphinic acid or a pharmaceutically acceptable form thereof selected from the group consisting of a salt, a solvate and a combination thereof.

5. A compound according to claim 1 which is (3-amino-2-oxopropyl) phosphinic acid
or a stereoisomer thereof, or a pharmaceutically acceptable form of either selected from the group consisting of a salt, a solvate and a combination thereof.

6. A compound according to claim 1 which is (2S)-(3-amino-2-hydroxypropyl)phosphinic acid or a pharmaceutically acceptable form thereof selected from the group consisting of a salt, a solvate and a combination thereof.

7. A compound according to claim 1 which is (2R)-(3-amino-2-hydroxypropyl)phosphinic acid or a pharmaceutically acceptable form thereof selected from the group consisting of a salt, a solvate and a combination thereof.

8. A method for the inhibition of transient lower oesophageal sphincter relaxations which method comprises administering to a subject suffering from said condition a pharmaceutical preparation comprising a compound according to any one of claims 1, 2–4 and 5–7.

9. A method for the treatment of gastro-oesophageal reflux disease which method comprises administering to a subject suffering from said condition a pharmaceutical preparation comprising a compound according to any one of claims 1, 2–4 and 5–7.

10. A method for the treatment of regurgitation in infants which method comprises administering to a subject suffering from said condition a pharmaceutical preparation comprising a compound according to any one of claims 1, 2–4 and 5–7.

11. A pharmaceutical formulation comprising as active ingredient a therapeutically acceptable amount of a compound according to any one of claims 1,2–4 and 5–7 optionally in association with diluents, excipients or inert carriers.

* * * * *